(12) United States Patent
Hudgins

(10) Patent No.: US 7,618,457 B2
(45) Date of Patent: Nov. 17, 2009

(54) DEVICES AND METHODS FOR DISC NUCLEUS REPLACEMENT

(75) Inventor: Robert Garryl Hudgins, Burnsville, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 427 days.

(21) Appl. No.: 11/201,837

(22) Filed: Aug. 10, 2005

(65) Prior Publication Data

US 2007/0038301 A1 Feb. 15, 2007

(51) Int. Cl.
*A61F 2/44* (2006.01)
(52) U.S. Cl. .................................... 623/17.12
(58) Field of Classification Search ............. 623/16.11, 623/17.11–17.16; 606/90
See application file for complete search history.

(56) References Cited

U.S. PATENT DOCUMENTS

| | | | |
|---|---|---|---|
| 6,187,048 B1 | 2/2001 | Milner et al. | |
| 6,224,630 B1* | 5/2001 | Bao et al. | 623/17.16 |
| 6,332,894 B1 | 12/2001 | Stalcup et al. | |
| 6,371,990 B1* | 4/2002 | Ferree | 623/17.16 |
| 6,428,576 B1* | 8/2002 | Haldimann | 623/17.16 |
| 6,530,933 B1* | 3/2003 | Yeung et al. | 606/151 |
| 6,592,625 B2* | 7/2003 | Cauthen | 623/17.16 |
| 6,733,533 B1 | 5/2004 | Lozier | |
| 6,893,466 B2* | 5/2005 | Trieu | 623/17.16 |
| 6,969,404 B2* | 11/2005 | Ferree | 623/17.11 |
| 2003/0078661 A1* | 4/2003 | Houfburg | 623/17.11 |
| 2003/0195628 A1 | 10/2003 | Bao et al. | |
| 2003/0220649 A1 | 11/2003 | Bao et al. | |
| 2004/0083002 A1 | 4/2004 | Belef et al. | |
| 2006/0247781 A1* | 11/2006 | Francis | 623/17.16 |

FOREIGN PATENT DOCUMENTS

| | | |
|---|---|---|
| DE | 3922203 C1 | 10/1990 |
| WO | WO 0044319 A1 | 8/2000 |
| WO | WO 02/17825 A2 | 3/2002 |
| WO | WO 030047472 A1 | 6/2003 |
| WO | WO 2004026190 A2 | 4/2004 |
| WO | WO 20040052248 A1 | 6/2004 |
| WO | WO 2005009299 A1 | 2/2005 |

OTHER PUBLICATIONS

European Patent Office, International Search Report and Written Opinion for PCT/US2006/030785, 15 pgs., dated Apr. 5, 2007.
European Patent Office, Partial International Search Report for PCT/US2006/030785, 5 pp, Dec. 29, 2006.

* cited by examiner

*Primary Examiner*—Eduardo C Robert
*Assistant Examiner*—Tara R George
(74) *Attorney, Agent, or Firm*—Crompton, Seager & Tufte, LLC.

(57) ABSTRACT

The present disclosure concerns implants to at least partially replace the nucleus of a spinal disc. In one embodiment, a prosthetic structure is provided which includes a bag operable to contain at least one internal implant within the bag. In another embodiment, a sinusoidal-shaped structure made of a flexible material is provided with various unique configurations to act as the internal implant and once released from a stretched or compressed configuration resumes nearly its original shape. In one embodiment, for delivery, a sinusoidal-shaped structure may be in a reduced amplitude state. In another embodiment, a sinusoidal-shaped structure is alternately woven from one end to the other with a second sinusoidal-shaped structure.

48 Claims, 4 Drawing Sheets

DEVICES AND METHODS FOR DISC NUCLEUS REPLACEMENT

BACKGROUND

Embodiments of the present invention relate generally to disc replacement therapy. More particularly, embodiments of the present invention relate to devices, materials and methods that can be used in disc replacement therapy procedures.

Generally, a healthy mammalian spine includes a series of vertebrae with discs located in an intervertebral space between each of the adjacent vertebrae. The discs of the spine function to allow motion and to distribute vertical axial loads on the spine. Discs generally are formed of an annulus fibrosis, which creates a disc perimeter, and a gel-like nucleus material, which is positioned within the annulus fibrosis. The healthy nucleus acts essentially as an incompressible fluid within a container, the annulus. The nucleus is compressed by the vertical forces on the spine and deforms horizontally to distribute the vertical load into the disc annulus.

Certain spinal disorders can cause damage to the disc. For example, one type of spinal disorder is a "herniated disc," which occurs when a portion of the disc nucleus presses out a hole or herniated region in the surrounding annulus. When this happens, the extruded nucleus material can press on nerves in the spinal region, causing back or spinal pain.

Pain can vary in herniated disc patients from very little to debilitating, and movement can, at times, intensify the pain. Numbness and muscle weakness also may occur. If the pressure on the nerve root is great, the legs can be paralyzed. Further, if the cauda equina (the bundle of nerves extending from the bottom of the cord) is affected, control of bladder and bowels also can be lost. If these serious symptoms develop, medical attention is required immediately.

Some patients with herniated discs recover without corrective measures. Many others, however, require surgery. In severe cases, surgery may require removal of all of a disc and perhaps part of a vertebra. For example, treatments for herniated or ruptured discs can include spinal fusion and/or disc nucleus replacement. Spinal fusion includes removal of the disc nucleus and in some cases the annulus. The adjacent vertebrae then is fixed in position to the open space often times by some structure placed between the two vertebrae. A bone growth supplement then can be placed within this space to stimulate the adjacent bone and/or vertebrae to grow into this space causing them to merge or fuse together. The disadvantage to this procedure, however, is the loss of the shock absorbing feature and mobility of a healthy disc.

Another possible treatment for herniated or ruptured discs is disc nucleus replacement. In this treatment, the disc nucleus is fully or partially removed and replacement material or structures are placed within the annulus. The replacement material or structures provide at least some load bearing function of the former nucleus and allows spinal motion at the effected disc level.

While some nucleus replacement materials and methods currently are known, further improvements are needed. Thus, needs exist for nuclear disc replacement materials and structures that can be introduced through minimally invasive procedures and also remain within the nuclear space without a future risk of extrusion.

SUMMARY

In one embodiment, the present invention relates to a prosthetic structure for replacement of at least a portion of the intervertebral disc nucleus. Use of this structure allows the annulus fibrosis to remain substantially intact. The device includes a bag structure made from a flexible material having a cavity therein. The bag structure includes an opening that is in communication with the cavity, and which is adapted to allow an interior implant structure to be placed into the cavity. Further, the bag structure is adapted to remain within an intervertebral disc space without extrusion from the space when combined with the interior implant material.

In some embodiments, the flexible material of the bag structure can comprise a woven or non-woven polymeric fiber, a woven or non-woven metallic material, or a combination thereof. In some embodiments, the flexible material of the bag structure can include a semi-permeable flexible material. In some embodiments, the flexible material of the bag structure can include a material having an elastic or viscoelastic property.

In one embodiment, the present invention comprises a prosthetic implant structure including a device formed of multiple periodic portions of flexible material, wherein the periodic portions of flexible material intersect a longitudinal axis at two points. In some embodiments, the device can be made of a woven or non-woven polymeric fiber, a woven or non-woven metallic material, or a combination thereof.

Further, in another particular embodiment, the present invention can comprise the prosthetic bag structure discussed above configured to receive an interior implant structure formed of multiple periodic portions of material each intersecting a longitudinal axis at two points. Thus, in accordance with this particular embodiment, the interior implant device is flexible such that when stretched in a longitudinal direction, the device flattens sufficiently so that it can fit through an opening of the prosthetic bag structure. Further, the interior implant device can be sufficiently elastic and possess shape memory, such that when released from a stretched position, the device returns substantially to its original shape. Thus, when the interior implant structure is placed within the prosthetic bag structure, it resumes an unstretched position, which prevents it from exiting the opening of the prosthetic bag structure.

In yet another embodiment of the present invention, an interior implant structure may include two or more sinusoidal-shaped devices, in which at least a second sinusoidal-shaped device is attached to or interlaced or interwoven with a first sinusoidal-shaped device. In this particular embodiment, each of the sinusoidal-shaped devices is located in a different plane from one another.

In yet another embodiment, the present invention relates to a method for implanting a prosthetic structure into an intervertebral space. In one embodiment, the method includes removing at least a portion of a disc nucleus to create a cavity within the disc annulus. Next, a bag structure having an opening for receiving an interior implant structure is inserted into the cavity. Once inserted, the bag structure is expanded in the cavity. Then, an interior implant structure is inserted into the opening in the bag structure. In one embodiment, the interior implant structure is formed of multiple periodic portions of flexible material. In other embodiments, other implant structures can be used. After the implant structure is placed in the bag structure, the opening in the bag structure is sealed so that the interior implant structure cannot be extruded from the intervertebral space.

A more complete understanding of the present invention may be derived by referring to the detailed description of preferred embodiments and claims when considered in connection with the figures.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

FIG. 1b is a cross-sectional view of the intervertebral disc nucleus prosthetic bag structure of FIG. 1a;

DETAILED DESCRIPTION

Embodiments of the present invention relate generally to devices, materials and methods for replacing at least a portion of a intervertebral disc nucleus. More particularly, embodiments of the present invention relate to disc nucleus prosthesis structures, including prosthesis bag structures, implant structures, and a combination of prosthesis bag structures and implant structures. While various prosthetic structures discussed herein are presented with reference to replacement of part or all of a human disc, embodiments of the present invention have application beyond human disc replacement. For example, the prosthetic structures discussed herein could be used in or with discs for any suitable vertebrate animal that might need or justify a disc replacement.

Figure 1A:
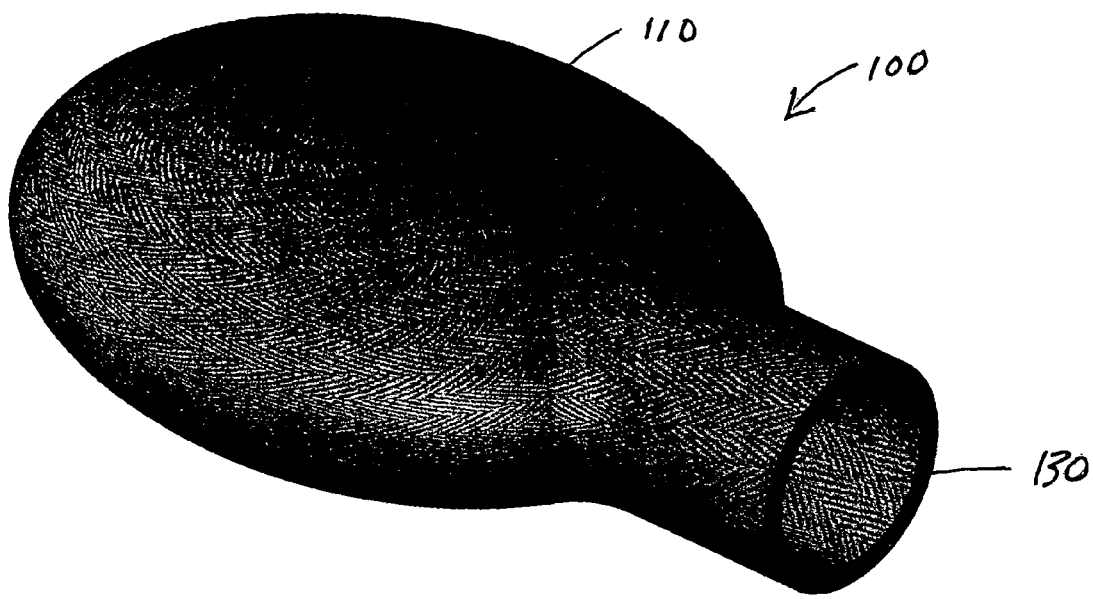
FIG. 1a is a three dimensional view of an intervertebral disc nucleus prosthetic bag structure in accordance with one embodiment of the present invention.
Figure 1B:
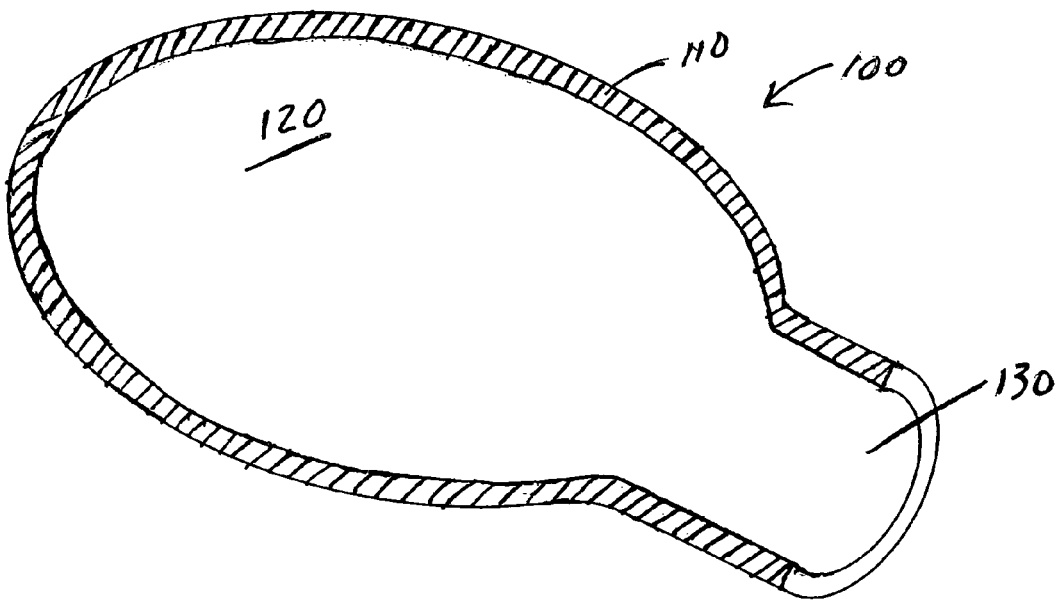

Referring now to FIG. 1, one embodiment of the present invention comprises an intervertebral disc nucleus prosthetic bag structure 100 that may be used for replacing all or part of a diseased, damaged or otherwise non-functional intervertebral disc nucleus. In the illustrated embodiment, bag structure 100 includes an outer body 110, an interior cavity 120, and opening 130 for receiving, for example, an interior implant structure or material.

In accordance with one embodiment of the invention, bag structure 100, and in particular, outer body 110 is formed of a flexible material. In some other embodiments, the bag structure 100, and in particular, outer body 110 is formed of a semi-permeable flexible, resilient, elastic or viscoelastic material. The later materials can have a time dependent deformation quality that dissipates some mechanical energy; thus, there is a viscoelastic quality to the material in some of these examples. Therefore, the bag structure can be compressed, so that it can be implanted in an annulus fibrosis cavity using a delivery device, such as a catheter or the like. Once inserted into the intervertebral space, the bag structure can be released from the delivery device, so that it returns to its relaxed unstretched state. Implantation of the bag structure will be discussed in more detail below.

In one embodiment, outer body 110 of bag structure 100 is formed of an immunologically inert material that is compatible with the environment found within a mammalian body, and in particular, within an intervertebral disc. As one skilled in the art will appreciate, the immunologically inert material does not induce any significant response by the immune system when the structure is implanted into a subject. Bag structure 100 can be formed of one or more materials, including in some embodiments, one or more composite materials. In addition, the outer body 110 of bag structure 100 can be formed from one or more layers of material.

In some embodiments, bag structure 100 can be formed of one or more different materials, which exhibit semi-permeable, flexible, resilient and/or elastic properties. That is, the material of bag structure 100 is such that it is capable of being easily stretched, expanded or compressed, and then resuming its former shape or close to its former shape. For example, in one embodiment, a bag structure 100 can be formed from a woven or non-woven polymeric fiber material, such as, an aramid material (e.g., Kevlar™, Nomex™, Twaron™, etc.), a polyester fiber material, an ultra high molecular weight polyethylene fiber material, a nylon fiber material, a cellulose fiber material, a polyurethane fiber material, or a polyacrylonitrile based fiber material. In some embodiments the polymeric fiber material can be woven or configured into a 2-dimensional or 3-dimensional fabric configuration.

In another embodiment of the present invention, bag structure 100 can be made and/or formed from a metallic material, such as nitinol, stainless steel (eg. heat-treated PH 17-7 stainless steel fabric) or the like. In still other embodiments, bag structure 100 can be made and/or formed from metallic fibers woven into a fabric-type material. In some embodiments, the fabric-type material can be a 2-dimensional or 3-dimensional fabric configuration.

In further embodiments, bag structure 100 can be made of a combination of materials. For example, one combination might be a combination of a polymeric fiber and a metallic material; e.g., an aramid material (e.g., Kevlar or the like) and a metallic material (e.g., nitinol, stainless steel).

In another embodiment of the present invention, bag structure 100 can be made of a semi-permeable, flexible, composite material, such as a composite comprised of an elastomeric or hydrogel matrix material and a polymeric fiber, a metal fiber or wire, or a ceramic fiber. Examples of suitable matrix materials that can be used to form bag structure 100 include, but are not limited to, a natural or synthetic polymer matrix material, an elastomer, a flexible polyolefin polymer, an elastomeric matrix material, or a hydrogel material.

Discussed above are various examples of classes of materials that can be used to form bag structure 100. Other specific materials that can be used to make bag structure 100 include, but are not limited to, polyaramid fibers, such as Kevlar 49, Kevlar 149- or the like, ultra high molecular weight, highly oriented, highly crystalline polyethylene (e.g., Dyneema or Spectra 900 or Spectra 1000), polyester fibers, such as Dacron, silk fiber, elastin fiber, elastomeric materials for (polyurethane or other thermoplastic elastomer), fused PTFE (Polytetrafluoroethylene), expanded PTFE of generally high tenacity fibers or other high strength woven or non-woven fibers or fabrics. It is also contemplated that any embodiment of the present invention may be accompanied by vertebroolasty to increase the strength of any weakened vertebrae including but not limited to disease, aging or injury.

In some embodiments, an interior implant material and/or structure is placed into bag structure 100 so that the combination of the bag structure and interior implant material create a resilient disc nucleus prosthesis. In some embodiments, the interior implant material or structure conforms to at least a portion of the interior cavity of the bag structure, thus creating the resilient prosthetic structure. In accordance with some embodiments of the invention, the interior implant material or device can be, for example, a hydrogel implant, a spiral implant, a biological implant, the implant structure discussed below, or any other suitable disc nucleus implant material or device. In one embodiment, the interior implant material and/or device can be, for example, the spiral implant devices disclosed in U.S. Pat. No. 5,919,235, which is incorporated herein by reference in its entirety. Further, in other embodiments, the sinusoidal-shaped structural device discussed below can be implanted or positioned within bag structure 100. The implantation of this device in a bag structure will be discussed in more detail below.

Figure 2:
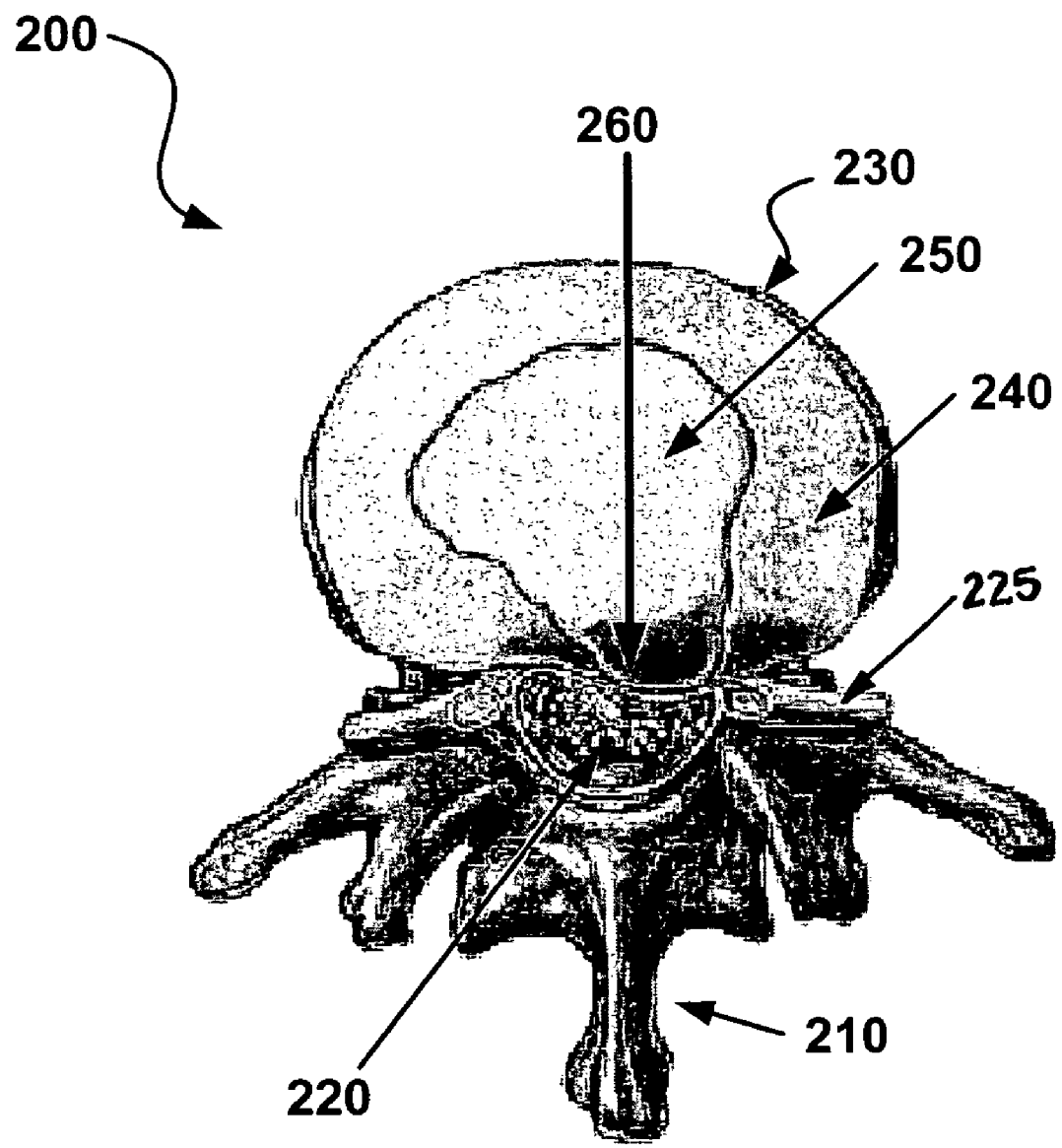
FIG. 2 is a cross-sectional view of a spinal column showing a herniated disc.

Referring now to FIG. 2, a cross-sectional view of a spinal column 200 having a herniated disc or damaged disc is shown. In the illustrated embodiment, the cross-section shows a vertebrae 210, a spinal cord 220 with nerve roots 225, and a disc 230, having an annulus 240 and a disc nucleus 250. As is illustrated by location 260 in FIG. 2, a herniated disc occurs when disc nucleus 250 protrudes an opening or weakness in annulus 240, putting pressure on spinal cord 220 and/or nerve roots 225. When this occurs, one remedy is to remove the protruding disc nucleus and replace it with a prosthetic nucleus structure and/or material. As one skilled in the art will appreciate, a disc nucleus replacement procedure includes, first removing at least a portion of the disc nucleus. In addition, as one skilled in the art will appreciate, a disc replacement procedure includes estimating the size and conformation required to replace the damaged disc area. In one embodiment of the present invention, the entire disc can be removed and replaced if warranted. In some embodiments, partial and/or total disc replacement can require anchoring of the intervertebral prosthetic structure such as encouraging tissue ingrowth into a structure (e.g. 2- or 3-dimensional weave structure). These procedures are known in the art, and thus, will not be discussed in detail herein.

After at least a portion of the disc nucleus is removed, the prosthetic structure and/or material can be placed within the annulus where the nucleus material was removed. In accordance with one embodiment of the present invention, once the nucleus material is removed, a delivery device (e.g., a cannula or other catheter device) can be used to introduce bag structure 100 into the annulus cavity. In one embodiment, bag structure 100 can be stretched and/or compressed and then attached to the delivery device so that it can be delivered through an opening in the disc annulus into the disc nucleus region. For example, in one embodiment, bag structure 100 is compressed into a cannula or onto a catheter, and then delivered into the nucleus region using a balloon catheter delivery technique, or the like. After the bag structure 100 is delivered into the nucleus region, it is released. In some embodiments, upon release, bag structure 100 will expand to substantially its uncompressed original shape.

In other embodiments, a balloon device (e.g., balloon catheter device) can be used to deploy bag structure 100 within the disc nucleus region. As one skilled in the art will appreciate, during a balloon catheter delivery procedure, a balloon catheter is used to place bag structure 100 within the disc nucleus, and then a balloon is inflated within the bag structure 100, causing the compressed bag structure to expand to its original or close to original shape. Once the bag structure is expanded, the balloon is deflated and then removed.

After bag structure 100 has been positioned within the disc nucleus region, an interior implant structure and/or material can be placed within the interior 120 of bag structure 100 for additional nucleus support. The interior implant structure and/or material can be introduced or positioned within interior 120 of bag structure 100 through opening 130 (see FIGS. 1a and 1b). Different delivery devices and/or methods may be used to insert the interior implant into the bag structure, and the delivery devices and/or methods used may differ depending on the type of implant material or structure used. After the interior implant material and/or structure is placed within bag structure 100, opening 130 of bag structure 100 then can be sealed or closed, thus holding the interior implant material and/or structure within the bag structure. As one skilled in the art will appreciate, any sealing or closing process and/or device can be used to seal the bag structure, such as suturing, clamping, tying, using a single directional opening valve or the like.

Figure 3A:
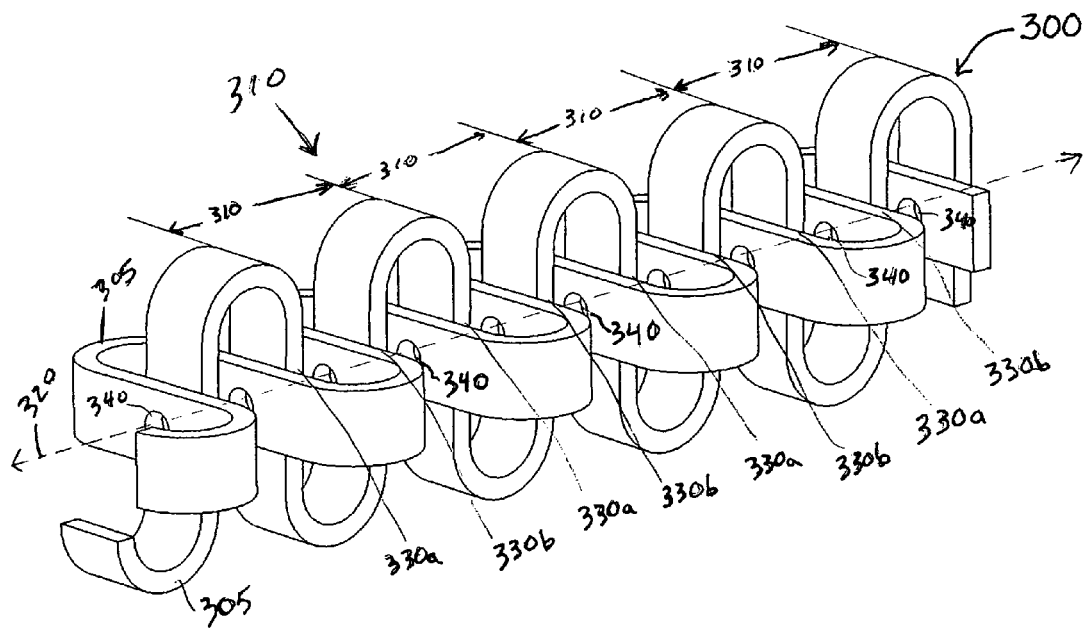
FIG. 3a is a three dimensional view of an implant structure in accordance with one embodiment of the present invention.
Figure 3B:
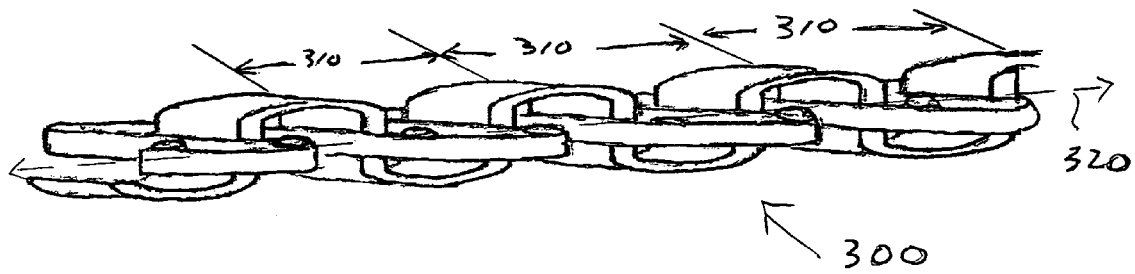
FIG. 3b is a three dimensional view of the implant structure shown in FIG. 3a, in a stretched configuration.

One aspect of the present invention relates to an interior implant structure, which can act as a disc nucleus replacement prosthesis, or at least as an interior portion of a disc nucleus prosthesis structure; one embodiment of which is illustrated in FIG. 3. In the illustrated embodiment, interior implant structure 300 comprises one or more sinusoidal-shaped structures 305. In accordance with this particular embodiment of the invention, each sinusoidal-shaped structure 305 comprises a plurality of periodic portions 310, which are formed of a flexible, resilient, elastic material. As illustrated in FIG. 3, each periodic portion 310 intersecting a longitudinal axis 320 of the interior implant structure 300 at two points, 330a and 330b. In one embodiment, the sinusoidal-shaped structures 305 is flexible, such that when stretched in a longitudinal direction (i.e., along axis 320), the structure sufficiently flattens or otherwise reduces the amplitude of each of the periodic portions 310, so that it can be placed within a disc nucleus region or holding structure within the disc nucleus region (e.g., bag structure 100, discussed above). FIG. 3b illustrates one embodiment of interior implant structure 300 (i.e., sinusoidal-shaped structures 305) in a stretched configuration.

Figure 4:
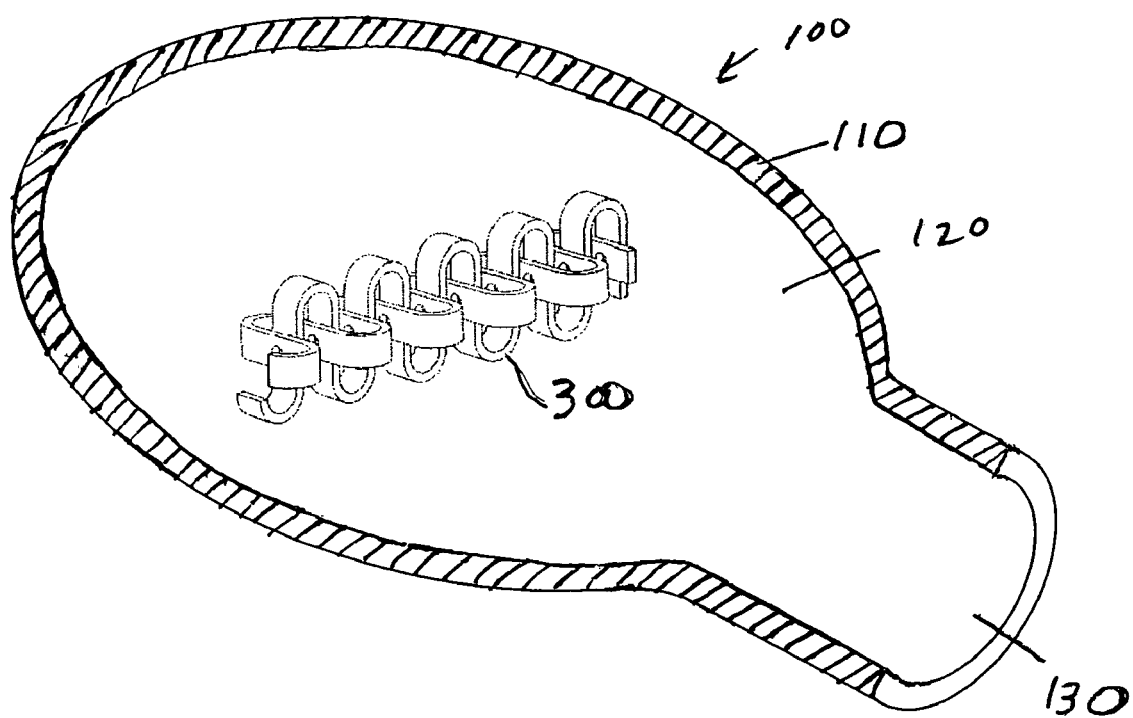
FIG. 4 is a cross-sectional view of one embodiment of an intervertebral disc nucleus prosthetic bag structure having an implant structure positioned therein in accordance with the present invention.

Further, sinusoidal-shaped implant structure 300 are formed of a flexible, resilient material, so that when released from a stretched position (typically, within the disc nucleus region, or in an implant holding structure), the device returns substantially to its original sinusoidal shape. In one embodiment of the present invention, the original sinusoidal shape of the device includes a configuration where the amplitude of at least one of the periodic portions of the sinusoidal shape when in an unstretched position is large enough to prevent the device from exiting the opening in the bag structure. FIG. 4 illustrates sinusoidal-shaped implant structure 300 positioned within bag structure 100, which is discussed in detail above.

As illustrated in FIG. 3, one embodiment of the invention can comprise multiple sinusoidal-shaped structures 305 positioned together, or otherwise interwoven with each other. The embodiment illustrated in FIG. 3 shows two sinusoidal-shaped structures 305 interwoven or otherwise joined and positioned in planes that are positioned at or near 90 degrees from one another. In other embodiments, two sinusoidal-shaped structures 305 can be positioned in different planes that are not necessarily perpendicular to one another. In still other embodiments, more than two sinusoidal-shaped structures 305 can be used.

In accordance with yet other embodiments of the invention, sinusoidal-shaped structures 305 can include holes 340 through the material at or near the center of the structures (i.e., at or near longitudinal axis 320). As discussed in more detail below, the holes can be used to accommodate an implantation or delivery device such as a cannula, catheter, etc.

As with bag structure 100 discussed above, some embodiments of interior implant structure 300 can be formed of an immunologically inert material that is compatible with the environment found within a mammalian body, and in particular, within an intervertebral disc. As one skilled in the art will appreciate, the immunologically inert material does not induce any significant response by the immune system when the structure is implanted into a subject. Further, as with bag structure 100, interior implant structure 300 can be formed of one or more materials, including in some embodiments, one or more composite materials. In addition, interior implant structure 300, and in particular, sinusoidal-shaped structures 305 can be formed from one or more layers of material.

In some embodiments, as with bag structure 100, sinusoidal-shaped structures 305 can be formed of one or more different materials, which exhibit flexible, resilient and/or elastic or viscoelastic properties. That is, the material of structures 305 is such that it is capable of being easily stretched, expanded or compresses, and then resuming its former shape or close to its former shape. For example, in one embodiment, structures 305 can be formed from a woven or non-woven polymeric fiber material, such as, an aramid material (e.g., Kevlar™, Nomex™, Twaron™, etc.), a polyester fiber material, an ultra high molecular weight polyethylene fiber material, a nylon fiber material, a cellulose fiber material, a polyurethane fiber material, or a polyacrylonitrile based fiber material. In some embodiments the polymeric fiber material can be woven or configured into a 2-dimensional or 3-dimensional fabric configuration.

Further, in other embodiments, sinusoidal-shaped structures 305 can be made and/or formed from a metallic material, such as nitinol, stainless steel or the like. In still other embodiments, structures 305 can be made and/or formed from metallic fibers woven into a fabric-type material. In some embodiments, the fabric-type material can be a 3-dimensional fabric configuration.

In further embodiments, sinusoidal-shape structures 305 can be made of a combination of materials. For example, one combination might be a combination of a polymeric fiber and a metallic material; e.g., an aramid material (e.g., Kevlar or the like) and a metallic material (e.g., nitinol, stainless steel).

In another embodiment of the present invention, sinusoidal-shaped structures 305 can be made of a flexible composite material, such as a composite comprising an elastomeric or hydrogel matrix material and a polymeric fiber, metal fiber or wire, or a ceramic fiber. Examples of suitable matrix materials that can be used to form structures 305 include, but are not limited to, a natural or synthetic polymer matrix material, an elastomer, a flexible polyolefin polymer, an elastomeric matrix material, or a hydrogel material.

Discussed above are various examples of classes of materials that can be used to form sinusoidal-shaped structures 305. Other specific materials that can be used to make structures 305 include, but are not limited to, polyaramid fibers, Kevlar 49, Kevlar 149 or the like, polyester fiber (e.g. Dacron), ultra high molecular weight, highly oriented, highly crystalline polyethylene (e.g., Dyneema), silk, elastin, elastomeric (polyurethane or other thermoplastic elastomer), fused PTFE (Polytetrafluoroethylene), expanded PTFE of generally high tenacity fibers or high strength non-woven fabric polyethylene, polyaryl, and PEEK (polyetheretherketone).

As discussed above, interior implant structures can be placed or positioned within a bag or containment structure, such as bag structure 100 discussed above. In some embodiments, interior implant structure 300 can be placed within bag structure 100 to form a resilient disc nucleus prosthetic structure (see FIG. 4). In one embodiment, one or more sinusoidal-shaped structures 305 can be placed within bag structure 100 to form the disc nucleus prosthesis. In other embodiments, one or more sinusoidal-shaped implant structures 305 can be placed in bag structure 100, along with one or more other implant materials such as hydrogel implant, a spiral implant, a therapeutic implant, a biologic implant, or a an in-situ curable material.

In one embodiment, interior implant structure 300 (i.e., sinusoidal-shaped structures 305) can be inserted into a bag structure (e.g., bag structure 100) located in the intervertebral cavity using an external delivery device, such as a cannula, a catheter, or other suitable delivery device. In accordance with one embodiment, a delivery device can be inserted through holes 340 in sinusoidal-shaped structures 305, and then the structures can be stretched along the delivery device to reduce the height or amplitude of the sinusoidal-shaped devices, as discussed above. Once the height of the structure is sufficiently reduced, it can be positioned or placed within the internal cavity 120 of bag structure 100, for example, through opening 130 in bag structure 100. Once inside the bag structure, interior implant structure 300 (i.e., sinusoidal structures 305) is released from the delivery device, which will allow structures 305 to expand back to or near its original shape, thus filling the bag structure and at least a portion of the disc nucleus regions.

In some embodiments, a coating agent can be applied to a bag structure (e.g., bag structure 100) and/or an interior implant structure (e.g., interior implant structure 300). In one embodiment, the coating agent may include one or more of hydrogel, a curable biomaterial that changes states once introduced to the intervertebral disc region (e.g., by chemical or heat promotion), elastomers (e.g., thermoset and thermoplastic), polyolefins, therapeutic agents (e.g., anti-bacterial or anti-fungal agents or biological agents). Biological agents can include, for example, tissue extracts, cells (e.g., bone derived cells), growth factors (e.g., platelet derived growth factor (PDGF)), proteins (e.g. the hormone calcitonin) or genes (e.g., nerve growth or bone growth promoting genes).

The foregoing discussion of the invention has been presented for purposes of illustration and description. It is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights, which include alternative embodiments, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An intervertebral prosthetic structure for replacement of at least a portion of an intervertebral disc nucleus, comprising:

a bag structure made from a flexible material having a cavity therein, the bag structure comprising an opening in communication with the cavity, wherein the opening is adapted to allow an interior implant structure to be placed into the cavity, wherein the bag is pre-formed prior to being inserted into an intervertebral space, the bag structured to be compressed for insertion into the intervertebral space, wherein the bag structure in combination with the interior implant structure is adapted to remain within an intervertebral disc space without extrusion from the space; and an interior implant structure including two or more interwoven sinusoidal-shaped structures, each sinusoidal-shaped structure including a length of flexible material defining a plurality of periodic portions, each periodic portion intersecting a longitudinal axis at two points, wherein a cross-sectional shape of the length of flexible material is substantially constant along the periodic portions.

2. The prosthetic structure of claim 1, wherein the flexible material comprises a semi-permeable material.

3. The prosthetic structure of claim 2, wherein the semi-permeable material comprises a woven or non-woven polymeric fiber.

4. The prosthetic structure of claim 3, wherein the polymeric fiber material comprises a polyester monofilament or multifilament yarn of 3-dimensional fabric configuration.

5. The prosthetic structure of claim 3, wherein the polymeric fiber material is selected from a group consisting of an aramid material, a polyester fiber material, an ultra high molecular weight polyethylene fiber material, a nylon fiber material, a cellulose fiber material, a polyurethane fiber material, and a polyacrylonitrile based fiber material.

6. The prosthetic structure of claim 2, wherein the semi-permeable flexible material comprises a woven or non-woven metallic material.

7. The prosthetic structure of claim 6, wherein the metallic material comprises nitinol.

8. The prosthetic structure of claim 1, wherein the flexible material comprises an elastic or viscoelastic material.

9. The prosthetic structure of claim 1, wherein the flexible material comprises a combination of a polymeric fiber and a metallic material.

10. The prosthetic structure of claim 1, wherein the flexible material comprises a composite material.

11. The prosthetic structure of claim 10, wherein the composite material comprises a polymeric fiber material in combination with a matrix material.

12. The prosthetic structure of claim 11, wherein the matrix material comprises an elastomeric or hydrogel matrix material.

13. The prosthetic structure of claim 1, wherein the flexible material is selected from a group consisting of nitinol, stainless steel, a natural or synthetic polymer, an elastomer, a flexible polyolefin polymer, an elastomeric matrix material, a hydrogel matrix material, and a hydrogel matrix material having a fiber-base reinforcement or combination thereof.

14. The prosthetic structure of claim 1, wherein the two or more sinusoidal-shaped structures of the interior implant structure have substantially the same shape, wherein one sinusoidal-shaped structure is disposed in a horizontal orientation and another sinusoidal-shaped structure is disposed in a vertical orientation.

15. The prosthetic structure of claim 1, wherein the bag structure is coated with an agent.

16. A prosthetic implant structure comprising a device formed of two or more interwoven sinusoidal-shaped structures, each sinusoidal-shaped structure including a length of flexible material defining a plurality of periodic portions, each periodic portion intersecting a longitudinal axis at two points, wherein a cross-sectional shape of the length of flexible material is substantially constant along the periodic portions.

17. The prosthetic implant structure of claim 16, wherein the device is structured to be inserted into a prosthetic bag structure, the device and the bag structure combination being operable to replace at least a portion of an intervertebral disc nucleus.

18. The prosthetic implant structure of claim 16, wherein the flexible material of the device is structured to stretch in a longitudinal direction and once stretched is structured to flatten sufficiently to fit through an opening.

19. The prosthetic implant structure of claim 18, wherein the opening comprises an opening within the disc or an opening within a bag structure.

20. The prosthetic implant structure of claim 18, wherein the flexible material of the device comprises an elastic or viscoelastic material wherein when released from a stretched position, the device returns substantially to its original shape.

21. The prosthetic implant structure of claim 16, wherein the device is configured so that an amplitude of at least one of the periodic portions in an unstretched position of the device is large enough to prevent the device from exiting an opening in the disc or bag structure.

22. The prosthetic implant structure of claim 16, wherein the flexible material comprises a woven or non-woven polymeric fiber material.

23. The prosthetic implant structure of claim 22, wherein the polymeric fiber material is a polyester monofilament or a polyester multifilament yarn comprising a 2-dimensional fabric configuration.

24. The prosthetic implant structure of claim 22, wherein the polymeric fiber material is a polyester monofilament or a polyester multifilament yarn comprising a 3-dimensional fabric configuration.

25. The prosthetic implant structure of claim 22, wherein the polymeric fiber material is selected from a group consisting of an aramid material, a polyester fiber material, an ultra high molecular weight polyethylene fiber material, a nylon fiber material, a cellulose fiber material, a polyurethane fiber material, and a polyacrylonitrile based fiber material.

26. The prosthetic implant structure of claim 16, wherein the flexible material comprises a woven or non-woven metallic material.

27. The prosthetic implant structure of claim 26, wherein the metallic material comprises nitinol or stainless steel.

28. The prosthetic implant structure of claim 16, wherein the flexible material comprises a combination of a polymeric fiber and a metallic material.

29. The prosthetic implant structure of claim 16, wherein the flexible material comprises a composite material.

30. The prosthetic implant structure of claim 16, wherein the two sinusoidal-shaped structures have substantially the same shape, wherein one sinusoidal-shaped structure is disposed in a horizontal orientation and another sinusoidal-shaped structure is disposed in a vertical orientation such that the two structures are oriented substantially perpendicular to one another.

31. The prosthetic implant structure of claim 16, wherein each of the sinusoidal-shaped structures comprises holes through the material near each of the points where the periodic portions intersect a longitudinal axis.

32. The prosthetic implant structure of claim 16, wherein the device is coated with an agent.

33. The prosthetic implant structure of claim 32, wherein the agent is selected from a group consisting of hydrogel, a curable biomaterial, an elastomer, a polyolefin, a therapeutic agent, a biological agent or combination thereof.

34. An intervertebral prosthetic structure comprising:
a bag having a cavity therein and an opening providing access to the cavity;
an interior implant structure located in the cavity, the interior implant structure comprising a length of flexible material defining a plurality of periodic portions of material, each periodic portion intersecting a longitudinal axis at two points, wherein the interior implant structure as a whole has a sinusoidal shape, wherein a cross-sectional shape of the length of flexible material is substantially constant along the periodic portions;
wherein an amplitude of a periodic portion in an unstretched position has a size which prevents the interior implant structure from exiting the opening in the bag.

35. The intervertebral prosthetic structure of claim 34, wherein the bag structure comprises a flexible material.

36. The intervertebral prosthetic structure of claim 34, wherein the material of the bag structure comprises a woven or non-woven metallic material.

37. The intervertebral prosthetic structure of claim 34, wherein the material of the interior implant structure comprises an elastic or viscoelastic material.

38. The intervertebral prosthetic structure of claim 34, wherein the material of the interior implant structure comprises a woven or non-woven polymeric fiber.

39. The intervertebral prosthetic structure of claim 34, wherein the material of the interior implant structure comprises a woven or non-woven metallic material.

40. The intervertebral prosthetic structure of claim 34, wherein the interior implant structure further comprises a second device being formed of a plurality of periodic portions of flexible material, each periodic portion intersecting a longitudinal axis at two points, and wherein each of the devices is oriented along a plane and the planes of the two devices intersect one another.

41. The prosthetic structure of claim 40, wherein the two devices are oriented substantially perpendicular to one another.

42. A method of implanting a prosthetic structure into an intervertebral space comprising:
removing at least a portion of a disc nucleus to create a cavity;
forming a bag structure, compressing the bag structure, and inserting the bag structure into the cavity, the bag structure comprising an opening for receiving an interior implant structure;
expanding the bag structure in the cavity;
inserting an interior implant structure into the opening in the bag structure, the interior implant including two or more interwoven devices, each device as a whole having a sinusoidal shape, each device being formed of a plurality of periodic portions of flexible material, each of the plurality of periodic portions intersecting a longitudinal axis at two points, wherein the periodic portions of each device are spaced and structured such that when a first device is disposed in a horizontal orientation, a second device can be interwoven in a vertical orientation, with the periodic portions of one device extending through the periodic portions of the other device; and
sealing the opening in the bag structure so that the interior implant structure cannot escape.

43. The method of claim 42, wherein the flexible material comprises an elastic or viscoelastic material.

44. The method of claim 42, wherein sealing the opening in the bag structure comprises sealing the opening using a draw string, a heat sealer, a single-directional opening valve, a suture or a clamp.

45. The method of claim 42, wherein expanding the bag structure comprises expanding the bag structure using a balloon catheter.

46. The method of claim 42, wherein the step of inserting the interior implant structure into the bag structure comprises:
stretching the interior implant structure in a longitudinal direction to reduce the amplitude of the periodic portions of the device to be able to fit the device into the opening of the bag structure;
inserting the interior implant structure into the bag structure; and
releasing the interior implant structure from the delivery device within the bag structure;
wherein when the interior implant structure is released, the flexible nature of the material causes the stretched device to substantially resume its unstretched state within the bag structure.

47. A method of delivering a prosthetic structure into an intervertebral space comprising:
removing at least a portion of a disc nucleus to create a cavity;
attaching an interior implant structure to a delivery device wherein the interior implant structure as a whole is sinusoidal shaped, the implant structure comprises a length of flexible material defining a plurality of periodic portions, each periodic portion intersecting a longitudinal axis at two points, wherein a cross-sectional shape of the length of flexible material is substantially constant along the periodic portions from a first end of the length of flexible material to a second end, and the delivery device being threaded through holes in the material near the intersecting points;
introducing the interior implant structure reversibly attached to the delivery device to the intervertebral space; and
releasing the interior implant structure from the delivery device;
wherein when releasing the interior implant structure from the delivery device an amplitude of a periodic portion in the interior implant structure has a size which prevents the interior implant structure from exiting the disc nucleus.

48. The method of claim 47, wherein the delivery device comprises a cannula.

* * * * *

UNITED STATES PATENT AND TRADEMARK OFFICE
CERTIFICATE OF CORRECTION

| | | |
|---|---|---|
| PATENT NO. | : 7,618,457 B2 | Page 1 of 1 |
| APPLICATION NO. | : 11/201837 | |
| DATED | : November 17, 2009 | |
| INVENTOR(S) | : Robert Garryl Hudgins | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 515 days.

Signed and Sealed this

Twenty-sixth Day of October, 2010

David J. Kappos
*Director of the United States Patent and Trademark Office*